US009702783B2

(12) United States Patent
DeAngelo et al.

(10) Patent No.: US 9,702,783 B2
(45) Date of Patent: Jul. 11, 2017

(54) AIR DATA PROBE WITH FLUID INTRUSION SENSOR

(71) Applicant: Rosemount Aerospace Inc., Burnsville, MN (US)

(72) Inventors: Timothy J. DeAngelo, Edina, MN (US); Richard Alan Schwartz, Faribault, MN (US); Curt A. Dykstra, Chaska, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 294 days.

(21) Appl. No.: 14/449,993

(22) Filed: Aug. 1, 2014

(65) Prior Publication Data
US 2016/0033356 A1 Feb. 4, 2016

(51) Int. Cl.
G01M 3/40 (2006.01)
G01N 27/06 (2006.01)
G01P 13/02 (2006.01)

(52) U.S. Cl.
CPC .............. G01M 3/40 (2013.01); G01N 27/06 (2013.01); G01P 13/025 (2013.01)

(58) Field of Classification Search
CPC ........ G01M 3/40; G01N 27/06; G01P 13/025; G01W 1/00
USPC ....................................................... 324/694
See application file for complete search history.

(56) References Cited

U.S. PATENT DOCUMENTS

| 3,665,760 A | 5/1972 | Pitches et al. |
| 4,264,901 A | 4/1981 | Petersen et al. |
| 5,361,633 A * | 11/1994 | Peet, II ................... G01P 13/02 73/1.75 |
| 5,731,507 A | 3/1998 | Hagen et al. |
| 6,941,805 B2 | 9/2005 | Seidel et al. |
| 8,365,591 B2 | 2/2013 | Golly |
| 2014/0373612 A1* | 12/2014 | Knittel ................. F02D 41/187 73/114.32 |

FOREIGN PATENT DOCUMENTS

GB          1247416       9/1971
WO     WO2012160349 A1  11/2012

OTHER PUBLICATIONS

Extended European Search Report for European Application No. 15178471.7, dated Sep. 29, 2015, 5 pages.

* cited by examiner

Primary Examiner — Jermele M Hollington
Assistant Examiner — Zannatul Ferdous
(74) Attorney, Agent, or Firm — Kinney & Lange, P.A.

(57) ABSTRACT

An air data probe includes a stationary housing assembly, an air data measurement unit, and a fluid sensing unit disposed proximate to an interface between the housing assembly and the air data measurement unit. The air data measurement unit is rotatable about a longitudinal axis of the air data probe, relative to the stationary housing assembly. The fluid sensing unit includes a second electrically conductive sensing surface physically and dielectrically spaced from a first sensing surface.

20 Claims, 7 Drawing Sheets

AIR DATA PROBE WITH FLUID INTRUSION SENSOR

BACKGROUND

The described subject matter relates generally to probes, and more specifically to air data probes and sensors.

Aircraft and other air vehicles utilize a number of probes, sensors, and other devices on the interior and exterior of the vehicle to monitor, detect and analyze various operational parameters. Some of these are located on or within the skin of the vehicle and can communicate with the onboard pilot or the remote operator of the vehicle. A number of such probes have movable sensing elements external to the aircraft. In order to maintain the needed sensitivity of the probe the interface between movable and fixed hardware is not hermetically sealed. Failure to fully seal the probe can allow intrusion of fluids, creating a potential situation for the sensing element(s) to lock up in flight.

Due to the risk of freezing, when moisture intrusion is merely suspected, a probe often requires removal from the vehicle, disassembly, and inspection for moisture prior to returning to service. Often a probe is taken out of service, disassembled, and inspected only to find that fluids have not infiltrated the unit. This can reduce availability and increase maintenance costs for the air vehicle, for example, when a worker improperly installs or fails to install protective covers over the probes prior to wash-down.

SUMMARY

An air data probe includes a stationary housing assembly, an air data measurement unit, and a fluid sensing unit disposed proximate to an interface between the housing assembly and the air data measurement unit. The air data measurement unit is rotatable about a longitudinal axis of the air data probe, relative to the stationary housing assembly. The fluid sensing unit includes a second electrically conductive sensing surface physically and dielectrically spaced from a first sensing surface.

A method for sensing fluid intrusion includes collecting at least a portion of an intruding fluid at an exterior location along an interface between a stationary housing assembly and a rotatable air data measurement unit. The fluid is directed to a fluid sensing unit disposed at an interior location proximate to the interface between the housing assembly and the air data measurement unit. An electrical resistance value is measured in the fluid sensing unit between a first electrically conductive sensing surface physically and dielectrically spaced from a second electrically conductive sensing surface.

DETAILED DESCRIPTION

Figure 1:
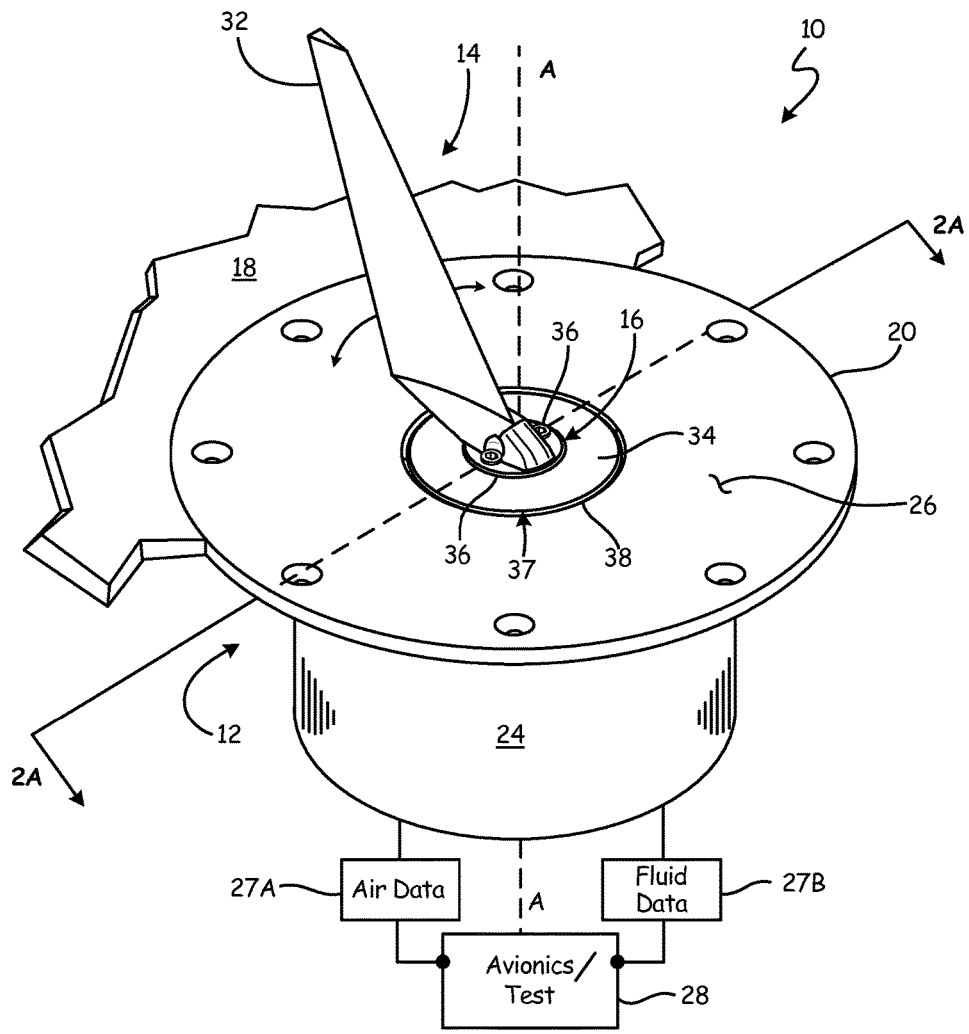
FIG. 1 is a perspective view of an example air data probe.

FIG. 1 is a perspective view of air data probe assembly 10 including, generally, stationary housing assembly 12 and air data measurement unit 14. FIG. 1 also includes hub 16, aircraft 18, mounting plate 20, housing 24, mounting plate outer surface 26, air data 27A, fluid intrusion data 27B, avionics 28, sensing fin 32, cover plate 34, fasteners 36, interface 37, and exterior gap 38.

Air data measurement unit 14 can be rotatable about longitudinal probe axis A-A via hub 16 which is disposed generally on or within stationary housing assembly 12 and also centered about longitudinal probe axis A-A. Stationary housing assembly 12 is in turn fixed to an aircraft or other air vehicle (not shown) inward of aircraft skin 18. In an illustrative embodiment, air data probe assembly 10 can be a stand-alone angle of attack (AOA) transducer unit which directly measures and communicates a primary measurement or indication of the angle of attack of the air vehicle. In another non-limiting example, air data probe assembly 10 can be a multi-function air data sensor unit with both rotatable and stationary sensing features. On commercial aircraft, an AOA sensor unit or multi-functional sensor unit can be installed on a side of the fuselage such that longitudinal probe axis A-A is generally perpendicular to a longitudinal axis of the aircraft (not shown). However, it will be appreciated that the described subject matter, except where explicitly limited, is not restricted to such configurations. For example, it will also be appreciated that air data measurement unit 14 can additionally and/or alternatively incorporate one or more other aerodynamic structures to facilitate rotation relative to stationary housing assembly 12.

Figure 2A:
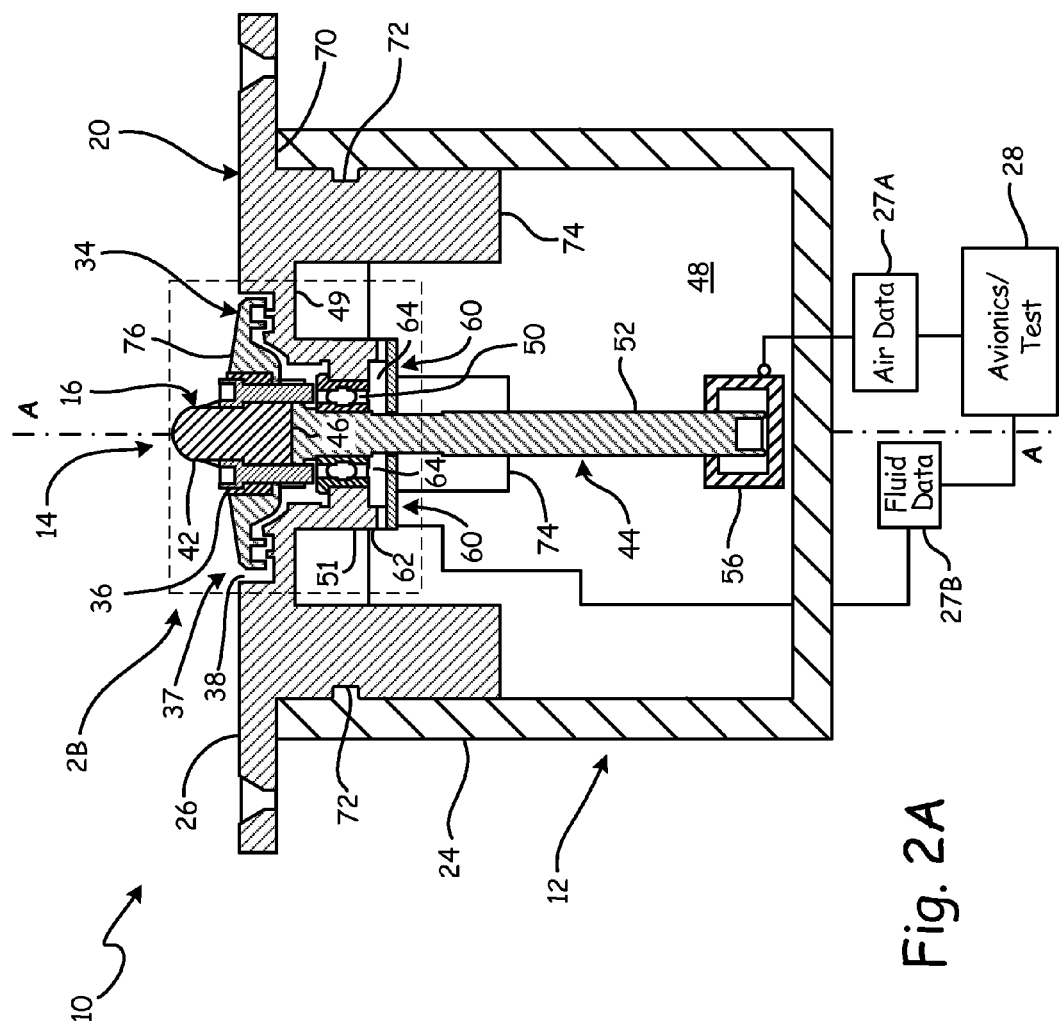
FIG. 2A shows a sectional view of the example air data probe taken across line 2A-2A of FIG. 1.

In the illustrative embodiment shown in FIG. 1, mounting plate 20 fits over an open end of housing 24, enclosing and defining a probe cavity (shown in FIG. 2A). Housing 24 can be cylindrical, frustoconical, or any other suitable shape so that housing 24 can fit within the available aircraft volume while retaining the various mechanical and electronic elements within the probe cavity. Depending on its location on the aircraft or air vehicle, mounting plate 20 can include either a substantially planar or a curved outer surface 26 adapted to be generally flush with aircraft skin 18 when properly installed.

In certain embodiments, air data probe 10 provides various information (e.g., air data 27A and fluid intrusion data 27B) to avionics 28. Avionics 28 are configured to gather, transmit, and/or analyze data or other signals (which can include air data 27A from air data probe 10) related to various aspects or parameters of flight to and from different nodes on the air vehicle and/or outside the air vehicle. Aircraft avionics 28 are not limited to a particular element or set of elements, and can be any conventional or inventive apparatus (e.g., a FADEC system).

Fluid intrusion data 27B can include specific data or signals related to unwanted intrusion of a fluid into air data probe 10. Fluid intrusion data 27B can be obtained from one or more fluid sensing units (shown in subsequent figures). Air data probe 10 can be configured to provide data 27B to avionics 28, but in certain embodiments, fluid intrusion data 27B can additionally or alternatively be provided to external test equipment (not explicitly shown) in communication with air data probe 10 having a fluid sensing unit.

In FIG. 1, rotation of air data measurement unit 14 can be facilitated by sensing fin (or vane) 32 mounted to hub 16.

Movement of the aircraft or air vehicle through the atmosphere induces rotation of sensing fin 32 about longitudinal probe axis A-A. Generally, relative movement and orientation of sensing fin 32 can be calibrated or otherwise configured in conjunction with aircraft avionics 28 to indicate one or more aspects or parameters of flight.

Cover plate 34 can be mounted concentrically between mounting plate 20 and hub 16 to reduce fluid intrusion into housing 24 and the probe cavity (shown in FIG. 2A). Mounting plate 20 and cover plate 34 each have a central aperture sized to receive the relevant component and allow rotation of air data measurement unit 14. Fasteners 36 can secure cover plate 34 (best seen in FIGS. 2A and 2B) so that cover plate 34 rotates along with hub 16 and sensing fin 32. To maintain free rotation of air data measurement unit 14 over a broad thermal range, interface 37 can include gaps or spaces between surfaces of stationary housing assembly 12 and rotatable air data measurement unit 14. Here, a small exterior gap 38 is visible between cover plate 34 and mounting plate 20, while interior gaps are shown in subsequent figures.

Many air data probes with rotatable sensor units are not hermetically sealed so as to reduce rotational friction over a wide range of air vehicle operating temperatures. However, failure to completely seal off the probe can allow unwanted intrusion and accumulation of fluids into the probe assembly, particularly around the gaps between the rotating unit(s) and the stationary housing. Most probes are designed to eject most incidental fluid intrusion such as that which results from precipitation. But one non-limiting example of unwanted fluid intrusion can occur when an aircraft or air vehicle is pressure-washed. Even here, external openings of probes and other components are ordinarily covered by a protective boot or other similar cover to prevent pressurized wash fluid from entering. However, covers sometimes fall off, are improperly installed, or are not installed at all. If the wash fluid or other pressurized fluid actually infiltrates the probe, it can freeze in flight or even prior to takeoff, causing rotatable portions of the probe to partially or completely lock up. In such cases, the risk of malfunction necessitates that such probes be removed from the aircraft and/or disassembled whenever fluid intrusion is merely suspected.

As shown in more detail in subsequent figures, air data probe assembly 10 can include one or more fluid sensing units disposed proximate to a base of hub 16. In certain embodiments, the fluid sensing unit(s) can include a fluid collection region adapted to collect fluid which has infiltrated air data probe 10 at or around location(s) between stationary housing assembly 12 and air data measurement unit 14. Such locations can include but are not limited to exterior gap 38. Disassembly and/or removal of air data probe 10 for cleaning and drying is thus required less often, typically only for regular maintenance and for when fluid intrusion is actually indicated. Thus one or more fluid intrusion sensor(s) allow air data probe 10 to more frequently remain intact and installed on the aircraft or air vehicle, increasing available uptime of the aircraft or other air vehicle.

Figure 2B:
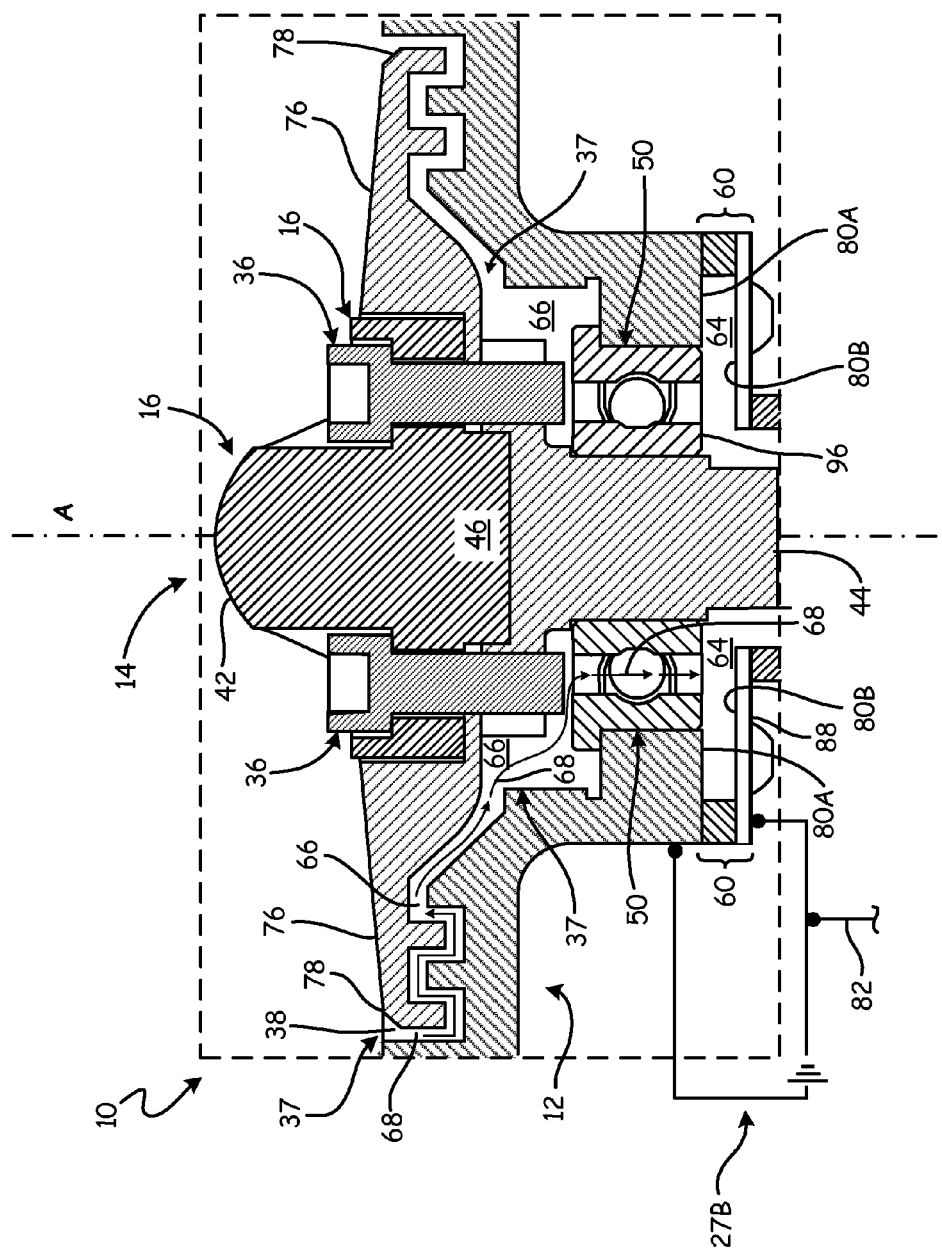
FIG. 2B is a magnified view of a portion of the air data probe from FIG. 2A showing a first example embodiment of a fluid sensing unit at an inner side of a mounting plate.

FIG. 2A is a cross-sectional view of air data probe 10 taken across line 2A-2A of FIG. 1, while FIG. 2B is a magnified view of a central portion of FIG. 2A. FIGS. 2A and 2B show stationary housing assembly 12, air data measurement unit 14, hub 16, mounting plate 20, housing 24, mounting plate outer side 26, air data 27A, fluid intrusion data 27B, cover plate 34, fasteners 36, interface 37, exterior gap 38, hub outer side 42, shaft 44, hub inner side 46, probe cavity 48, mounting plate inner side 49, bearing assemblies 50, hub flange 51, shaft inner end 52, angle resolver 56, fluid sensing unit 60, hub flange base 62, fluid collection region 64, gaps 66, fluid intrusion path 68, housing opening 70, housing fitting 72, mounting flanges 74, cover plate outer surface 76, cover plate aperture 78, conductive surfaces 80A, 80B, circuit 82, spacer ring 86, conductive ring 88, and bearing race 89.

Air data measurement unit 14 includes hub 16 centered about longitudinal axis A-A of air data probe 10. Though sensing fin 32 (shown in FIG. 1) is omitted from FIGS. 2A and 2B for clarity, fin 32 can be suitably mounted to, and extends outwardly from, hub outer side 42. Sensing fin 32 can be fastened, bonded, joined, or integrally formed to hub outer side 42. Shaft 44 can also be suitably connected to, and extend generally inwardly from, hub inner side 46 into probe cavity 48. In this example, fasteners 36 join hub 16, cover plate 34, and shaft 44 for rotation about axis A-A.

Mounting plate inner side 49 can have one or more hub flanges or other projections 51 supporting hub 16 via bearing assemblies 50. In the example shown in FIGS. 2A and 2B, hub 16, sensing fin 32 (shown in FIG. 1), and shaft 44 can be supported by suitable bearing assemblies 50 (via hub flange 51) to allow free rotation of air data measurement unit 14. Inner end 52 of shaft 44 can extend into probe cavity 48 and can be in communication with one or more transducers also disposed in probe cavity 48. Via the transducer(s), angular rotation and/or position of sensing fin 32 can be calibrated or otherwise configured in either a conventional or an inventive manner in conjunction with aircraft avionics 28 to indicate one or more aspects or parameters of flight.

In the example of an AOA sensor probe, one such transducer disposed in probe cavity 48 can include angle resolver 56. Angle resolver 56 can be in optical, electromagnetic, and/or mechanical communication with shaft inner end 52 to sense the relative rotational or angular position of sensing fin 32 (shown in FIG. 1), and in turn, generate and/or transmit a signal corresponding to the air vehicle's angle of attack for processing by avionics 28.

FIGS. 2A and 2B also show fluid sensing unit 60 in fluid communication with possible intrusion location(s) around interface 37 which extends into and around air data probe 10 between stationary housing assembly 12 and air data measurement unit 14. Such locations can include but are not limited to exterior gap 38. Fluid sensing unit 60 can also be disposed proximate to interface 37 such as around base 62 of hub flange 51, inward of bearings 50. Here, fluid sensing unit 60 includes fluid collection region 64 adapted to collect any fluid which infiltrates air data probe 10, including fluid infiltration from exterior gap 38 and/or other locations around interface 37 between stationary housing assembly 12 and air data measurement unit 14.

FIG. 2B also indicates fluid intrusion path 68 extending between exterior gap 38 and fluid sensing unit 60. This can be a tortuous path along one or more interfaces 37 and/or gaps 66. Here, interface 37 includes gaps 66, defined by annular spaces between various overlapping projections and recesses formed in different elements of housing assembly 12 and air data measurement unit 14. Gaps 66, and the resulting dimensions of fluid intrusion path 68, are not shown to scale and have generally been enlarged for purposes of illustration only.

In this illustrative non-limiting example, unwanted fluid enters exterior gap 38 between an outer diameter of cover plate 34 and an inner diameter of mounting plate 20. The infiltrating fluid then travels inward into probe cavity 48, defined here by substantially cylindrical housing 24 and mounting plate 20 secured over opening 70 in a longitudinal end of housing 24. This combination of mounting plate 20 and housing 24 can be secured, for example, by housing fitting 72 with mounting flanges 74. Securing can be achieved using an o-ring or an interference fit, but any suitable arrangement can be used based on the overall geometry of air data probe 10.

As best seen in FIG. 2B, cover plate 34 also includes outer surface 76 that is substantially flush with outer side 26 of mounting plate 20, with aperture 78 formed through a center of cover plate 34. These elements can be adapted in various related configurations to permit free rotation of sensor fin 32 (and other elements of air data sensing unit 14) relative to stationary housing assembly 12, and about longitudinal axis A-A. Cover plate outer surface 76 may not be fully planar, either for aerodynamic reasons or to direct unwanted fluid away from exterior gap 38. Outer perimeter 78 of cover plate 34 may be tapered adjacent to outer surface 76 so as to further minimize actual infiltration of unwanted fluid into exterior gap 38.

Generally, fluid sensing unit 60 can be incorporated into various air data probes (such as but not necessarily limited to AOA transducer assemblies). At least a portion of the infiltrating fluid can be collected (e.g., by flowing along fluid intrusion path 68) in fluid collection space or region 64 defined between two electrically isolated conductive surfaces 80A, 80B (best seen in FIG. 2B). Collected fluid bridges the otherwise isolated surfaces 80A, 80B by replacing the air normally occupying the intervening fluid collection space 64. Thus measuring a change in electrical resistance between normally isolated surfaces 80A, 80B (from a dry or other baseline state) will most often indicate unwanted fluid intrusion. This can be done, for example, by connecting the two structures defining surfaces 80A, 80B to one or more electrical circuits 82 such that resistance between surfaces 80A, 80B can be measured and compared to the resistance between surfaces 80A, 80B in a dry or other baseline state.

Figure 3:
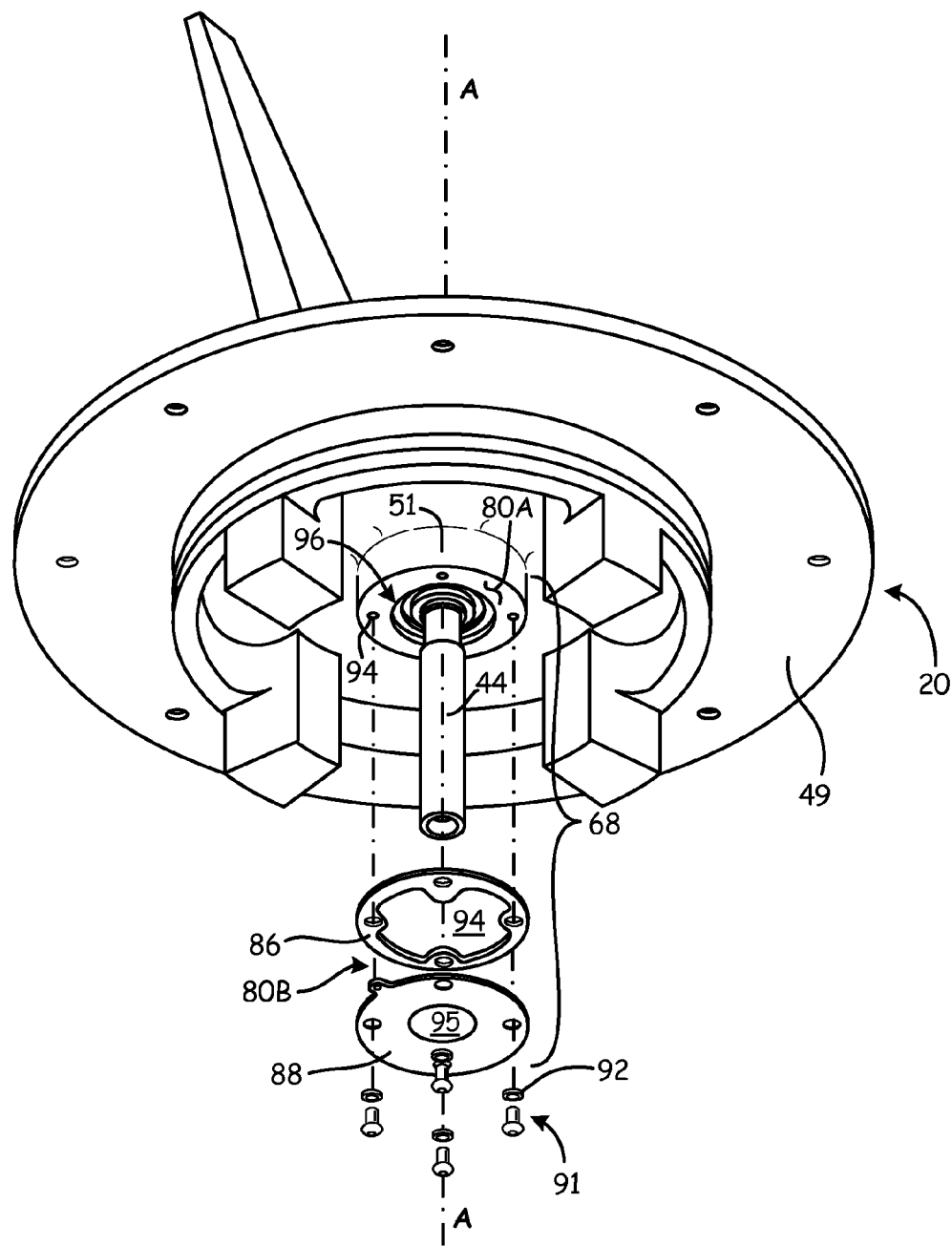
FIG. 3 includes an exploded bottom view of the fluid sensing unit and mounting plate shown in FIGS. 2A and 2B.

As best seen in FIG. 3, surface 80A can include a surface of mounting plate inner side 49, while surface 80B can include a surface of conductive ring 88, which is separated from hub flange 51 via dielectric spacer ring 86. Intruding fluid then passes through bearing assembly 50 (race 89) or other breathing features (not shown) into collection space 64 where it can be detected.

FIG. 3 is an exploded view of a portion of air data probe 10 intended to show details of first fluid sensing unit embodiment 60. FIG. 3 also includes mounting plate 20, mounting plate inner side 49, bearing assembly 50, hub flange 51, conductive surfaces 80A, 80B, spacer ring 86, conductive ring 88, bearing races 89, fasteners 91, insulating grommets 92, fastener apertures 93, spacer central aperture 94, and conductive ring central aperture 95.

Fluid sensing unit 60 can be implemented about inner side 49 of mounting plate 20. Generally, a dielectric spacer is fastened or otherwise secured between conductive surfaces 80A, 80B. In the non-limiting illustrative embodiment shown in FIG. 3, spacer ring 86 and conductive ring 88 are fastened to hub flange 51 such that spacer ring 86 dielectrically separates ring conductive surface 80B (best seen in FIG. 2B) from bottom side conductive surface 80A. While a plurality of fasteners 91 and insulating grommets 92 can be received into apertures 93, it will be appreciated that various other suitable combinations of conductive and insulating fasteners, washers, grommets, and the like can be used to electrically isolate rings 86, 88 (and in turn conductive surfaces 80A, 80B).

Conductive ring 88 has a similar or identical outer diameter to spacer ring 86, but its central aperture 95 is smaller than that of spacer ring central aperture 94. Both apertures 94, 95 are of a size which will at least accommodate shaft 44. Thus spacer ring 86 dielectrically and physically separates conductive ring 88 from hub flange 51, allowing fluid to be collected and sensed inward of bearing races 89, defining fluid collection region 64 (shown in FIGS. 2A-2B).

In other words, a first electrically conductive sensing surface can include conductive surface 80A on inner side 49 of mounting plate 20 (here, a surface of hub flange 51). A second electrically conductive sensing surface can include a surface of conductive (e.g., metallic) ring 88 fastened to inner side 49 of mounting plate 20. As a result, a second electrically conductive sensing surface can include surface 80B (best seen in FIG. 2B) of conductive ring 88, and be spaced from the first sensing surface (conductive surface 80A) via spacer ring 86.

Figure 4:
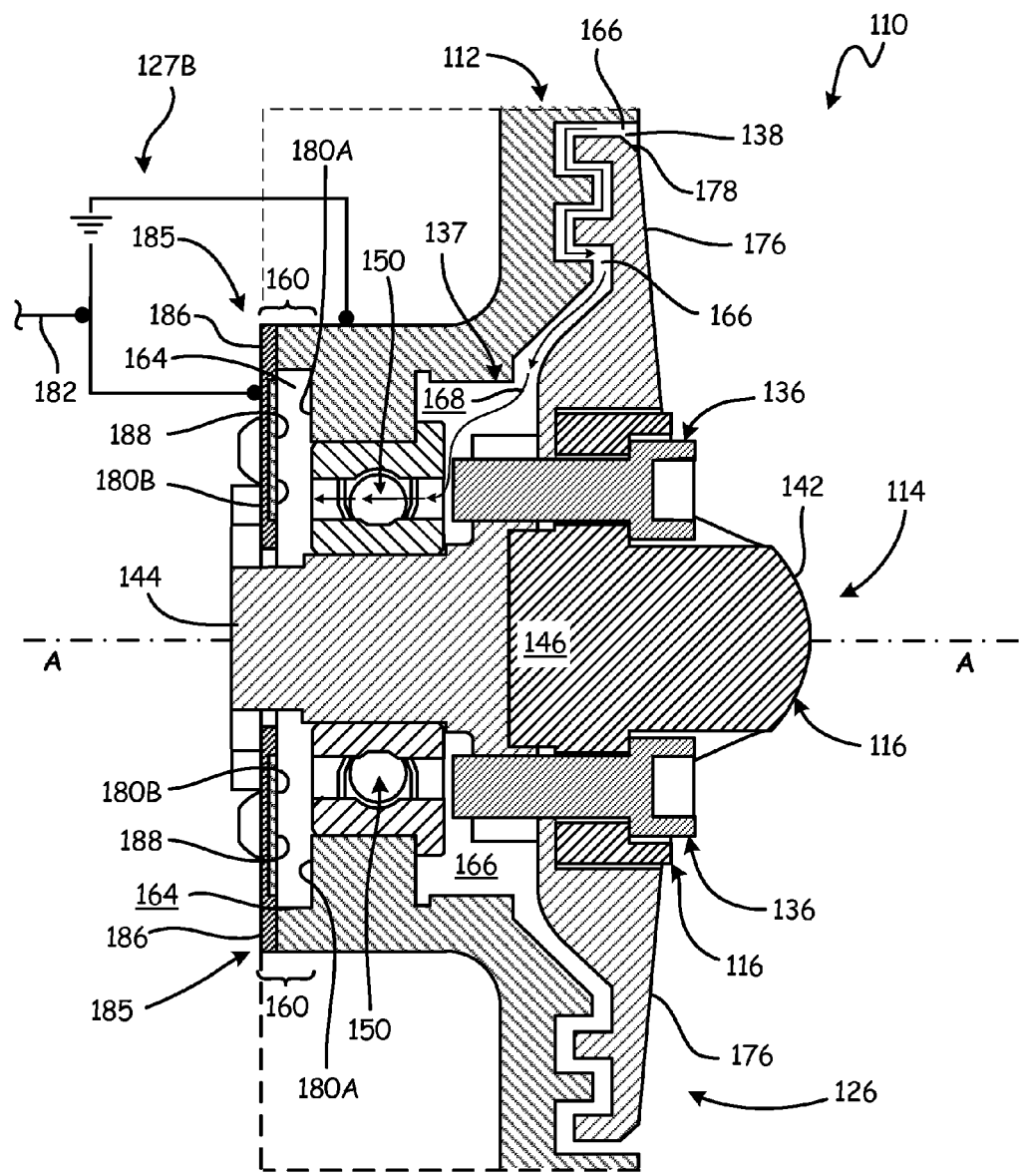
FIG. 4 shows a second example embodiment of a fluid sensing unit and an inner side of a mounting plate.

FIG. 4 shows a second example embodiment of a fluid sensing unit in which a single structure can incorporate both a second electrically conductive surface and a dielectric component to isolate the second surface from a first electrically conductive surface.

FIG. 4 shows a comparable view to FIG. 2B, and incorporates a number of similar elements. Air data probe 110 includes stationary housing assembly 112 and air data measurement unit 114. Fasteners 136 can secure cover plate 134 to hub 116 such that outer surface 176 is substantially flush with outer side 126 of mounting plate 120 (opposite inner side 149). Air data probe 110, including fluid sensing unit 160, is in communication via circuit 182 to provide fluid intrusion data 127B to avionics and/or external test equipment (not shown in FIG. 4). Fluid sensing unit 160 can also be in fluid communication with possible intrusion location(s) proximate to interface 137 (separating stationary housing assembly 112 and rotatable air data measurement unit 114). The intrusion locations can include exterior gap 138.

Fluid collection region 164 is adapted to collect any unwanted fluid which infiltrates air data probe 110 via fluid intrusion path 168, which can be a tortuous path extending along one or more interfaces 137 with gaps 166. In FIG. 4, gaps 166 can be defined between various mating projections and recesses formed in adjacent surfaces of mounting plate 120 and cover plate 134, as well as other gaps 166 separating strut 144 from bearing assembly 150. Aperture 178 can be formed through a center of cover plate 134 connect sensor fin 132 (shown in FIG. 5A) as well as hub 116 to strut 144. Outer perimeter 178 of cover plate 134 can be tapered adjacent to outer surface 176 (substantially flush with mounting plate outer side 126) so as to reject unwanted fluid and minimize infiltration.

Similar to the first example embodiment, at least a portion of the infiltrating fluid can be collected along fluid intrusion path 168 to fluid collection space or region 164 defined between two electrically isolated conductive surfaces 180A, 180B. Collected fluid bridges the otherwise isolated surfaces 180A, 180B by replacing the air normally occupying the intervening fluid collection space 164. Thus similar to the first example embodiment, unwanted fluid intrusion can be detected by measuring a difference in electrical resistance between normally isolated surfaces 180A, 180B. Again, the two structures defining surfaces 180A, 180B can serve as electrodes with the resistance measured therebetween. But as best seen in FIGS. 5A and 5B, a single combination ring 185 can provide both conductive surface 180B and dielectric spacer 186.

Figure 5A:
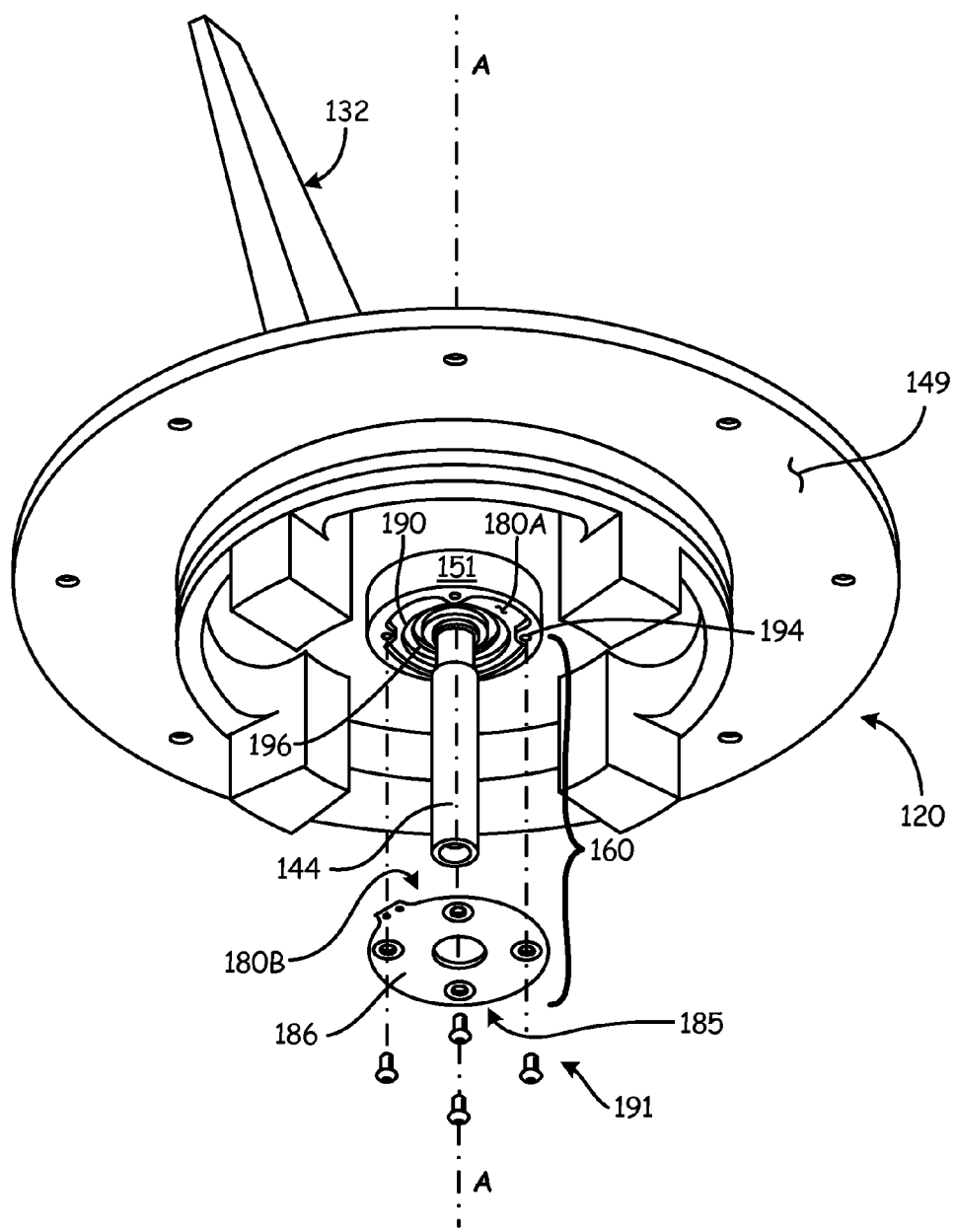
FIG. 5A is an exploded bottom view of the fluid sensing unit and mounting plate shown in FIG. 4.
Figure 5B:
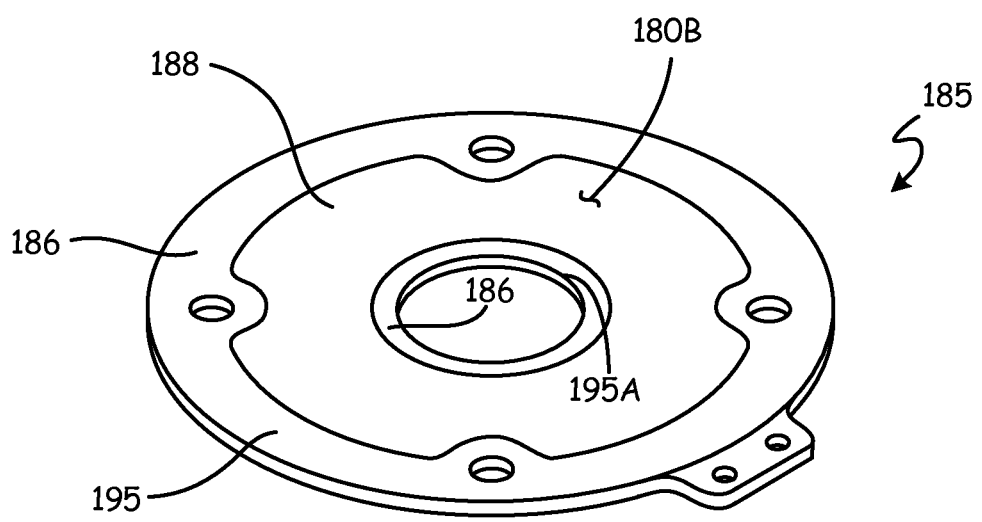
FIG. 5B shows a second side of the sensing board from FIG. 5A.

FIG. 5A is an exploded view of the second example embodiment utilizing combination ring 185 with dielectric spacer portion 186. FIG. 5B shows an inverse side of combination ring 185 with conductive portion 188.

Combination ring 185 can be directly fastened (via conductive or nonconductive fasteners 191) to inner side 149 of mounting plate 120. Similar to the first example embodiment, a conductive surface of hub flange 151 can define first conductive surface 180A in the second example embodiment. Here, however, second conductive surface 180B can be provided by conductive portion 188 of combination ring 185, which remains dielectrically separated from first conductive surface 180A via spacer portion 186.

In certain embodiments, to provide physical separation between first conductive surface 180A and second conductive surface 180B, pocket 190 can be recessed into hub flange 151 about bearing race 189. Combination ring 185 can thus be fastened so that leakage current would have to pass through either dielectric spacer 186 or fluid collection region 164 (shown in FIG. 4) to travel between hub flange 151 and conductive ring portion 188. In this way, first conductive surface 180A can include a base of pocket 190, while second conductive surface 180B can include a surface of conductive ring portion 188 facing pocket 190.

Dielectric spacer 186 can be any suitable electrically insulating substrate. As best seen in FIG. 5B, a relatively thin conductive ring portion 188 can be disposed concentrically between its inner edge 195A and outer edge 195B. In certain embodiments of combination ring 185, dielectric spacer 186 can include substrate material for a printed wiring board (PWB). The PWB substrate can form a substantial majority of combination ring 185, with a thin metallic plating defining conductive ring portion 188 (and second conductive surface 180B). With a printed wiring board in place of a more general dielectric substrate material, the PWB can include various circuitry (not shown) related to operation of air data probe 110. In certain of these example embodiments, resistance of one or both conductive surfaces 180A, 180B can be measured more directly and require fewer external connections.

A method for sensing fluid intrusion in an air data probe is also illustrated with reference to the figures. Fluid can be collected at an interface (e.g., interface 37 or interface 137) between a stationary housing assembly and a rotatable air data measurement unit. This interface can include, for example, exterior gap 38 (best seen in FIG. 2B) or 138 (best seen in FIG. 4). The fluid can be directed along a tortuous fluid intrusion path, for example, path 68 (best seen in FIG. 2B) or 168 (best seen in FIG. 4) to a fluid sensing unit (e.g., unit 60 in FIG. 2B or 160 in FIG. 4) disposed inside the air data probe. And as shown in the accompanying figures, the tortuous path can extend generally along a plurality of annular spaces or gaps 66/166 between the stationary housing assembly and the rotatable air data measurement unit. A space between first and second sensing surfaces can define a fluid collection and sensing region 64/164.

An electrical resistance value can be measured in the fluid sensing unit (e.g., resistance between first and second conductive sensing surfaces which are physically and dielectrically spaced apart in a fluid sensing region). Measured resistance value(s) can be compared (e.g., internally, by avionics 28, and/or by external test equipment) to one or more values to determine a likelihood of fluid contamination. In one example, the measured resistance can be compared to a predetermined, calculated, or estimated resistance value between the first and second conductive surfaces which corresponds to a dry or other baseline condition. The measured value can additionally and/or alternatively be compared to a minimum acceptable electrical resistance value, which can correspond to a maximum acceptable fluid contamination or intrusion level. Resistance can either be measured directly or differentially (e.g., by determining a net difference in resistance from each structure to electrical ground). Comparing can include determining whether the measured electrical resistance value is less than the baseline and/or the minimum electrical resistance value, and upon so determining, an indication can be provided (e.g., by avionics 28 and/or the external test equipment) which corresponds to unwanted fluid intrusion into the probe.

Discussion of Possible Embodiments

The following are non-exclusive descriptions of possible embodiments of the present invention.

An air data probe includes a stationary housing assembly, an air data measurement unit, and a fluid sensing unit disposed proximate to an interface between the housing assembly and the air data measurement unit. The air data measurement unit is rotatable about a longitudinal axis of the air data probe, relative to the stationary housing assembly. The fluid sensing unit includes a second electrically conductive sensing surface physically and dielectrically spaced from a first sensing surface.

The air data probe of the preceding paragraph can optionally include, additionally and/or alternatively, any one or more of the following features, configurations and/or additional components:

An air data probe according to an exemplary embodiment of this disclosure, among other possible things includes a stationary housing assembly; an air data measurement unit rotatable about a longitudinal axis of the air data probe, relative to the stationary housing assembly; and a fluid sensing unit disposed proximate to an interface between the housing assembly and the air data measurement unit, the fluid sensing unit comprising a first electrically conductive sensing surface; and a second electrically conductive sensing surface physically and dielectrically spaced from the first sensing surface.

A further embodiment of the foregoing air data probe, wherein the housing assembly comprises: a housing having at least one opening and a mounting plate secured over the opening in the housing to define a probe cavity; wherein the mounting plate includes an outer side adapted to be substantially flush with an air vehicle skin when the air data probe is installed.

A further embodiment of any of the foregoing air data probes, wherein the air data measurement unit comprises: a hub disposed about the longitudinal axis of the air data probe; a sensing fin mounted to an outer side of the hub; and a shaft connected to an inner side of the hub, and extending into a probe cavity.

A further embodiment of any of the foregoing air data probes, wherein the air data measurement unit further comprises a cover plate fastened to the hub and the strut for rotation with the sensing fin about the longitudinal axis.

A further embodiment of any of the foregoing air data probes, wherein the air data probe further comprises a tortuous fluid collection path, at least a portion of which is defined by a plurality of annular spaces between overlapping projections and recesses disposed along the interface between the air data measurement unit and the housing assembly.

A further embodiment of any of the foregoing air data probes, wherein the tortuous fluid intrusion path extends between an external location along the interface, and a fluid collection space defined proximate to the resistive fluid sensing unit.

A further embodiment of any of the foregoing air data probes, wherein the air data probe further comprises a dielectric spacer ring fastened to an inner side of the mounting plate; and a conductive metal ring fastened over the dielectric spacer ring such that a surface of the metal ring is physically and dielectrically spaced from the inner side of the mounting plate; wherein the first sensing surface includes a surface on the inner side of the mounting plate, and the second sensing surface includes a surface of the metal ring physically and dielectrically spaced from the first sensing surface.

A further embodiment of any of the foregoing air data probes, wherein the air data probe further comprises a combination ring fastened to an inner side of the mounting plate, the combination ring including a dielectric substrate portion having a first side with a conductive metal ring portion formed concentrically between inner and outer edges of the dielectric substrate; wherein the combination ring is fastened with the first side facing the inner side of the mounting plate and such that only the dielectric substrate portion contacts the inner side of the mounting plate, for dielectrically spacing the conductive metal ring portion from the first sensing surface.

A further embodiment of any of the foregoing air data probes, wherein the inner side of the mounting plate includes a pocket formed on an inner side of the mounting plate adapted to physically and dielectrically space the conductive metal ring portion from the first sensing surface.

A further embodiment of any of the foregoing air data probes, wherein the dielectric substrate portion is also adapted to form a substrate for a printed wiring board.

A further embodiment of any of the foregoing air data probes, wherein a space between the first sensing surface and the second sensing surface defines a fluid collection and sensing region for the fluid sensing unit.

A method for sensing fluid intrusion includes collecting at least a portion of an intruding fluid at an exterior location along an interface between a stationary housing assembly and a rotatable air data measurement unit. The fluid is directed to a fluid sensing unit disposed at an interior location proximate to the interface between the housing assembly and the air data measurement unit. An electrical resistance value is measured in the fluid sensing unit between a first electrically conductive sensing surface physically and dielectrically spaced from a second electrically conductive sensing surface.

The method of the preceding paragraph can optionally include, additionally and/or alternatively, any one or more of the following features, configurations and/or additional components:

A method according to an exemplary embodiment of this disclosure, among other possible things includes collecting at least a portion of an intruding fluid at an exterior location along an interface between a stationary housing assembly and a rotatable air data measurement unit; directing the fluid to a fluid sensing unit disposed proximate to an interface between the housing assembly and the air data measurement unit; and measuring an electrical resistance value in the fluid sensing unit, the electrical resistance value measured between a first electrically conductive sensing surface physically and dielectrically spaced from a second sensing surface.

A further embodiment of the foregoing method, further comprising: comparing the measured electrical resistance value to at least one of a baseline electrical resistance value and a minimum acceptable electrical resistance value, the at least one value corresponding to a maximum acceptable fluid contamination level.

A further embodiment of any of the foregoing methods, further comprising: upon determining that the measured electrical resistance value is less than the baseline electrical resistance value or the minimum electrical resistance value, providing an indication corresponding to unwanted fluid intrusion into the transducer assembly.

A further embodiment of any of the foregoing methods, wherein the interface includes a tortuous path extending generally along a plurality of annular spaces between the stationary housing assembly and the rotatable air data measurement unit.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:
1. An air data probe comprising:
a stationary housing assembly including a mounting plate secured over an opening in a housing to define a probe cavity;
an air data measurement unit rotatable about a longitudinal axis of the air data probe, relative to the stationary housing assembly;
a fluid sensing unit disposed proximate to an interface between the housing assembly and the air data measurement unit, the fluid sensing unit comprising:
a first electrically conductive sensing surface; and
a second electrically conductive sensing surface physically and dielectrically spaced from the first sensing surface; and
a combination ring fastened to an inner side of the mounting plate, the combination ring including a dielectric substrate portion having a first side with a conductive metal ring portion formed concentrically between inner and outer edges of the dielectric substrate;
wherein the combination ring is fastened with the first side facing the inner side of the mounting plate and such that only the dielectric substrate portion contacts the inner side of the mounting plate, for dielectrically spacing the conductive metal ring portion from the first sensing surface.

2. The air data probe of claim 1,
wherein the mounting plate includes an outer side adapted to be substantially flush with an air vehicle skin when the air data probe is installed.

3. The air data probe of claim 1, wherein the air data measurement unit comprises:
a hub disposed about the longitudinal axis of the air data probe;
a sensing fin mounted to an outer side of the hub; and
a shaft connected to an inner side of the hub, and extending into a probe cavity.

4. The air data probe of claim 3, wherein the air data measurement unit further comprises:
a cover plate fastened to the hub and the strut for rotation with the sensing fin about the longitudinal axis.

5. The air data probe of claim 1, further comprising:
a tortuous fluid collection path, at least a portion of which is defined by a plurality of annular spaces between overlapping projections and recesses disposed along the interface between the air data measurement unit and the housing assembly.

6. The air data probe of claim 5, wherein the tortuous fluid intrusion path extends between an external location along the interface, and a fluid collection space defined proximate to the fluid sensing unit.

7. An air data probe comprising:
a stationary housing assembly;
an air data measurement unit rotatable about a longitudinal axis of the air data probe, relative to the stationary housing assembly, the air data measurement unit having at least one sensor for measuring an aspect or a parameter of flight data; and
a fluid sensing unit disposed proximate to an interface between the housing assembly and the air data measurement unit, the fluid sensing unit comprising:
a first electrically conductive sensing surface connected to an electrical circuit;
a second electrically conductive sensing surface connected to the electrical circuit, the second electrically conductive sensing surface physically spaced and dielectrically spaced apart from the first sensing surface; and
a fluid collection space defined between the spaced apart first and second electrically conductive sensing surfaces;
wherein the fluid collection space is adapted to collect a portion of an infiltrating fluid other than air such that collected fluid bridges the fluid collection space between the first and second electrically conductive sensing surfaces, resulting in a change of resistance in the electrical circuit.

8. The air data probe of claim 1, wherein the inner side of the mounting plate includes a pocket formed on an inner side of the mounting plate adapted to physically and dielectrically space the conductive metal ring portion from the first sensing surface.

9. The air data probe of claim 1, wherein the dielectric substrate portion is also adapted to form a substrate for a printed wiring board.

10. The air data probe of claim 1, wherein a space between the first sensing surface and the second sensing surface defines a fluid collection and sensing region for the fluid sensing unit.

11. A method for sensing fluid intrusion, the method comprising:
collecting at least a portion of an intruding fluid other than air at an exterior location along an interface between a stationary housing assembly and a rotatable air data measurement unit;
directing the fluid to a fluid sensing unit disposed proximate to an interface between the housing assembly and the air data measurement unit, the fluid sensing unit comprising:
a first electrically conductive sensing surface connected to an electrical circuit;
a second electrically conductive sensing surface connected to the electrical circuit, the second electrically conductive sensing surface physically spaced and dielectrically spaced apart from the first sensing surface; and
a fluid collection space defined between the spaced apart first and second electrically conductive sensing surfaces, adapted to collect a portion of an infiltrating fluid other than air such that collected fluid bridges the fluid collection space; and
measuring an electrical resistance value in the fluid sensing unit between the first and second electrically conductive sensing surfaces, resulting in a change of resistance in the electrical circuit.

12. The method of claim 11, further comprising:
comparing the measured electrical resistance value to at least one of a baseline electrical resistance value and a minimum acceptable electrical resistance value, the at least one value corresponding to a maximum acceptable fluid contamination level.

13. The method of claim 12, further comprising:
upon determining that the measured electrical resistance value is less than the baseline electrical resistance value or the minimum electrical resistance value, providing an indication corresponding to unwanted fluid intrusion into the transducer assembly.

14. The method of claim 11, wherein the interface includes a tortuous path extending generally along a plurality of annular spaces between the stationary housing assembly and the rotatable air data measurement unit.

15. The air data probe of claim 7, further comprising:
a dielectric spacer ring fastened to an inner side of the mounting plate; and
a conductive metal ring fastened over the dielectric spacer ring such that a surface of the metal ring is physically and dielectrically spaced from the inner side of the mounting plate;
wherein the first sensing surface includes a surface on the inner side of the mounting plate, and the second sensing surface includes a surface of the metal ring physically and dielectrically spaced from the first sensing surface.

16. The air data probe of claim 7, wherein the air data measurement unit comprises:
a hub disposed about the longitudinal axis of the air data probe;
a sensing fin mounted to an outer side of the hub; and
a shaft connected to an inner side of the hub, and extending into a probe cavity.

17. The air data probe of claim 16, wherein the air data measurement unit further comprises:
a cover plate fastened to the hub and the strut for rotation with the sensing fin about the longitudinal axis.

18. The air data probe of claim 7, further comprising:
a tortuous fluid collection path, at least a portion of which is defined by a plurality of annular spaces between overlapping projections and recesses disposed along the interface between the air data measurement unit and the housing assembly.

19. The air data probe of claim 18, wherein the tortuous fluid intrusion path extends between an external location along the interface, and the fluid collection space defined proximate to the resistive fluid sensing unit.

20. The air data probe of claim 7, wherein the inner side of the mounting plate includes a pocket formed on an inner side of the mounting plate adapted to physically and dielectrically space the conductive metal ring portion from the first sensing surface.

* * * * *